(12) United States Patent
Groβ

(10) Patent No.: US 9,036,914 B2
(45) Date of Patent: May 19, 2015

(54) ARRANGEMENT WITH A ROTATABLE X-RAY DETECTOR

(75) Inventor: Stefan Groβ, Trabitz (DE)

(73) Assignee: Siemens Aktiengesellschaft, München (DE)

( * ) Notice: Subject to any disclaimer, the term of this patent is extended or adjusted under 35 U.S.C. 154(b) by 782 days.

(21) Appl. No.: 13/267,724

(22) Filed: Oct. 6, 2011

(65) Prior Publication Data

US 2012/0262154 A1    Oct. 18, 2012

(30) Foreign Application Priority Data

Oct. 7, 2010 (DE) .......................... 10 2010 042 123

(51) Int. Cl.
  *A61B 6/00*  (2006.01)
  *G01P 3/44*  (2006.01)

(52) U.S. Cl.
  CPC ............ *A61B 6/4458* (2013.01); *A61B 6/4441* (2013.01); *A61B 6/547* (2013.01)

(58) Field of Classification Search
  CPC .. A61B 6/4429; A61B 6/4435; A61B 6/4441; A61B 6/54; A61B 6/547; G01P 3/42; G01P 3/44; G01P 3/56
  USPC .................. 378/207, 208, 89–192, 196–198; 324/160, 166–175; 73/503.3, 73/504.01–504.18
  See application file for complete search history.

(56) References Cited

U.S. PATENT DOCUMENTS

| | | | |
|---|---|---|---|
| 5,899,401 A * | 5/1999 | Reimann et al. | 242/372 |
| 6,578,437 B1 * | 6/2003 | Moerbe | 73/862.328 |
| 7,418,081 B2 | 8/2008 | Holler et al. | |
| 7,901,135 B2 | 3/2011 | Fadler et al. | |
| 2002/0078808 A1 | 6/2002 | Jacobsen et al. | |
| 2004/0244209 A1 * | 12/2004 | Uehira et al. | 33/1 PT |
| 2008/0276706 A1 * | 11/2008 | Hartmann et al. | 73/504.04 |
| 2009/0010394 A1 * | 1/2009 | Watanabe | 378/145 |
| 2009/0154653 A1 * | 6/2009 | Fink et al. | 378/197 |
| 2009/0322001 A1 | 12/2009 | Luke et al. | |
| 2010/0006727 A1 * | 1/2010 | Boomgaarden et al. | 248/276.1 |
| 2011/0132087 A1 * | 6/2011 | Ohms et al. | 73/504.12 |
| 2012/0279489 A1 * | 11/2012 | Vogt | 126/606 |

FOREIGN PATENT DOCUMENTS

| | | |
|---|---|---|
| CN | 1984604 A | 6/2007 |
| CN | 101617944 A | 1/2010 |
| DE | 10 2004 057 003 A1 | 6/2006 |
| DE | 10 2004 057 004 A1 | 6/2006 |

(Continued)

OTHER PUBLICATIONS

German Office Action dated Apr. 14, 2011 for corresponding German Patent Application No. DE 10 2010 042 123.5-52 with English translation.

(Continued)

*Primary Examiner* — Jack Berman
*Assistant Examiner* — David E Smith
(74) *Attorney, Agent, or Firm* — Lempia Summerfield Katz LLC

(57) ABSTRACT

The present embodiments provide an arrangement with an X-ray detector that is driven by a rotation device. The arrangement includes a first rotational speed sensor and a second rotational speed sensor that determine a rotation of the X-ray detector. The first rotational speed sensor and the second rotational speed sensor are coupled via a connection device including a pre-tensioned torsion spring.

9 Claims, 3 Drawing Sheets

(56) References Cited

FOREIGN PATENT DOCUMENTS

| DE | 699 38 384 T2    | 4/2009 |
|----|------------------|--------|
| DE | 10 2009 026 123 A1 | 1/2010 |
| DE | 10 2008 030 828 B4 | 4/2010 |

OTHER PUBLICATIONS

Chinese Office Action dated Jul. 3, 2014 for corresponding Chinese Patent Application No. 201110300468.9.

* cited by examiner

ARRANGEMENT WITH A ROTATABLE X-RAY DETECTOR

This application claims the benefit of DE 10 2010 042 123.5, filed on Oct. 7, 2010.

BACKGROUND

The present embodiments relate to an arrangement with an X-ray detector that is driven by a rotation device.

X-ray systems used in the X-ray field (e.g., C-arm X-ray systems) may be equipped with a device for image rotation. In a C-arm X-ray system, a radiation source and a radiation detector are arranged on a C-shaped arm and may be moved jointly. The C-arm is guided about a patient by a robotic controller. In order to consistently obtain a desired image format when recording a series of images (e.g., a portrait or a landscape), even during a rotation of the C-arm, the ability to rotate the X-ray detector is provided. This makes it possible to adjust the image position using the rotatable X-ray detector during a rotation of the C-arm and to retain the selected image format. FIG. 1 shows a C-arm X-ray system 1 with a rotatable X-ray detector 4. A C-arm 2 bears an X-ray source 3 at one end and the X-ray detector 4, which may be rotated around a vertical axis of rotation 5, at an opposite end.

For precise adjustment of the image position, the respective position of the X-ray detector is to be determined. Rotational speed sensors are used for this purpose, via which an angle of rotation of an initiated rotation is measured in order to undertake control of the drive of the rotation device as feedback. For this purpose, a constant comparison of an actual position measured via the rotational speed sensor with a predetermined setpoint value is undertaken, and the rotational position is adjusted. An optimum measurement of the rotational position is based on measurement of the actual value of the rotational position.

To provide for the safety of an operator of an X-ray apparatus and of a patient to be examined with the X-ray apparatus, two rotational speed sensors may be used to measure the rotational position of the X-ray detector. A collision model for a device movement changes as a function of the respective position of the X-ray detector. To avoid collisions with a table or with the floor, the rotational position are to be reliably determined. Values of the first rotational speed sensor are constantly checked for plausibility using the second rotational speed sensor.

In clinical systems, the X-ray detector is attached to a pulley that is driven by a drive wheel attached to the pulley via a toothed belt. The drive wheel is driven by a motor. The drive wheel is also connected via a further toothed belt to a shaft, to which two rotational speed sensors are attached. The rotational position of the pulley may be determined via the two rotational speed sensors. If the toothed drive belt jumps as a result of mechanical overloading of the axis of rotation of the pulley, this is not detected by either of the two rotational speed sensors, since the two rotational speed sensors are only connected indirectly via the motor shaft to the axis of rotation of the pulley. As a result, an incorrect position of the X-ray detector remains uncorrected, since the axis of rotation of the pulley is not adjusted. A further problem lies in the fact that the two rotational speed sensors are not arranged directly on the shaft of the pulley to be controlled but are attached to the shaft of the pulley by elastic belts. The play in the pulleys also adversely affects the precision of the regulation of the drive based on the measured rotational positions.

SUMMARY AND DESCRIPTION

The present embodiments may obviate one or more of the drawbacks or limitations in the related art. For example, an improved device for determining a rotational position of an X-ray detector is provided.

The present embodiments include an arrangement with an X-ray detector that is driven by a rotation device. The arrangement includes a first rotational speed sensor and a second rotational speed sensor that determine a rotation of the X-ray detector. The first rotational speed sensor and the second rotational speed sensor are coupled via a connection device to a pre-tensioned torsion spring. In an advantageous manner, a direct, play-free connection of the first rotational speed sensor and the second rotational speed sensor to the rotation device is established via the pre-tensioning of the torsion spring.

In one embodiment, the torsion spring may be pre-tensioned such that the first rotational speed sensor and the second rotational speed sensor have a constant opposing moment. The constant opposing moment is responsible for the play-free connection of the first rotational speed sensor and the second rotational speed sensor to the rotation device.

In an advantageous manner, the connection device may include a first toothed wheel and a second toothed wheel that are coupled via the pre-tensioned torsion spring.

In one embodiment, the first rotation speed sensor may include a third toothed wheel and a fourth toothed wheel. The third toothed wheel is coupled to the first toothed wheel. In an advantageous manner, a play-free connection is established between the third toothed wheel and the first toothed wheel.

The second rotational speed sensor may include a fifth toothed wheel and a sixth toothed wheel. The fifth toothed wheel is coupled to the second toothed wheel. The advantage of this is that a play-free connection is established between the fifth toothed wheel and the second toothed wheel.

In one embodiment, the fourth toothed wheel and the sixth toothed wheel may be coupled by a pulley, to which the X-ray detector is attached.

In another embodiment, the pulley includes a seventh toothed wheel that is coupled to the fourth toothed wheel and to the sixth toothed wheel, such that teeth of the fourth toothed wheel and the sixth toothed wheel rest permanently on teeth of the seventh toothed wheel as a result of the pre-tensioned torsion spring. Using this arrangement of the toothed wheels, the first rotational speed sensor and the second rotational speed sensor are coupled directly and without play to the pulley to which the X-ray detector is attached. This provides that a violent jumping of a drive belt that connects a drive wheel to the pulley is detected by the first rotational speed sensor and the second rotational speed sensor. Thus, a rotational position may be adjusted in an advantageous manner. As a result, a deviation does not occur in the X-ray image.

In one embodiment, the first rotational speed sensor may be embodied as an absolute value sensor. An absolute value sensor is a device for measuring lengths or angles that is employed as a movement measuring device on machine tools and in measuring and testing devices in handling and automation technology.

Furthermore the second rotational speed sensor can be embodied as a potentiometer sensor. A potentiometer sensor is a known position sensor designed like a potentiometer and is employed to measure angles.

DETAILED DESCRIPTION OF THE DRAWINGS

Figure 1:
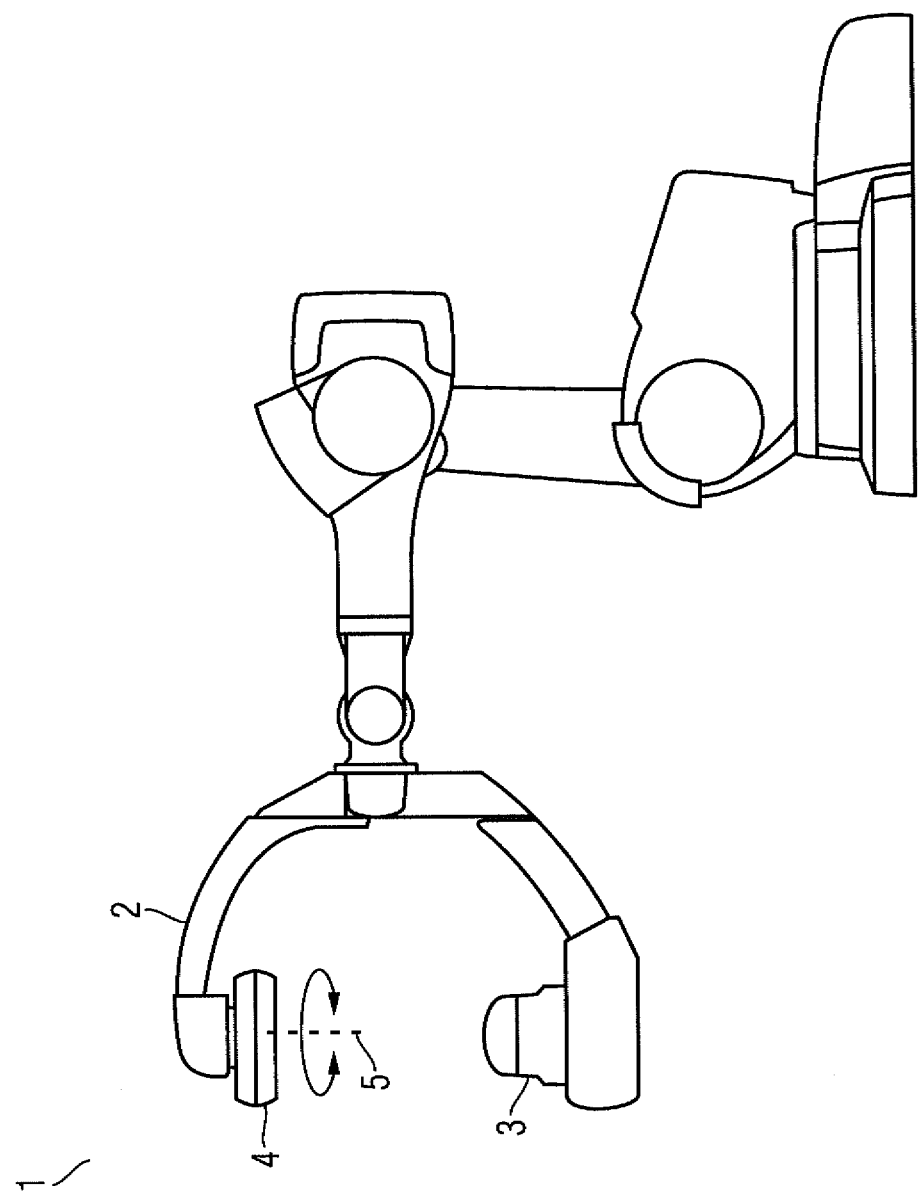
FIG. 1 shows a C-arm X-ray system with a rotatable X-ray detector.
Figure 2:
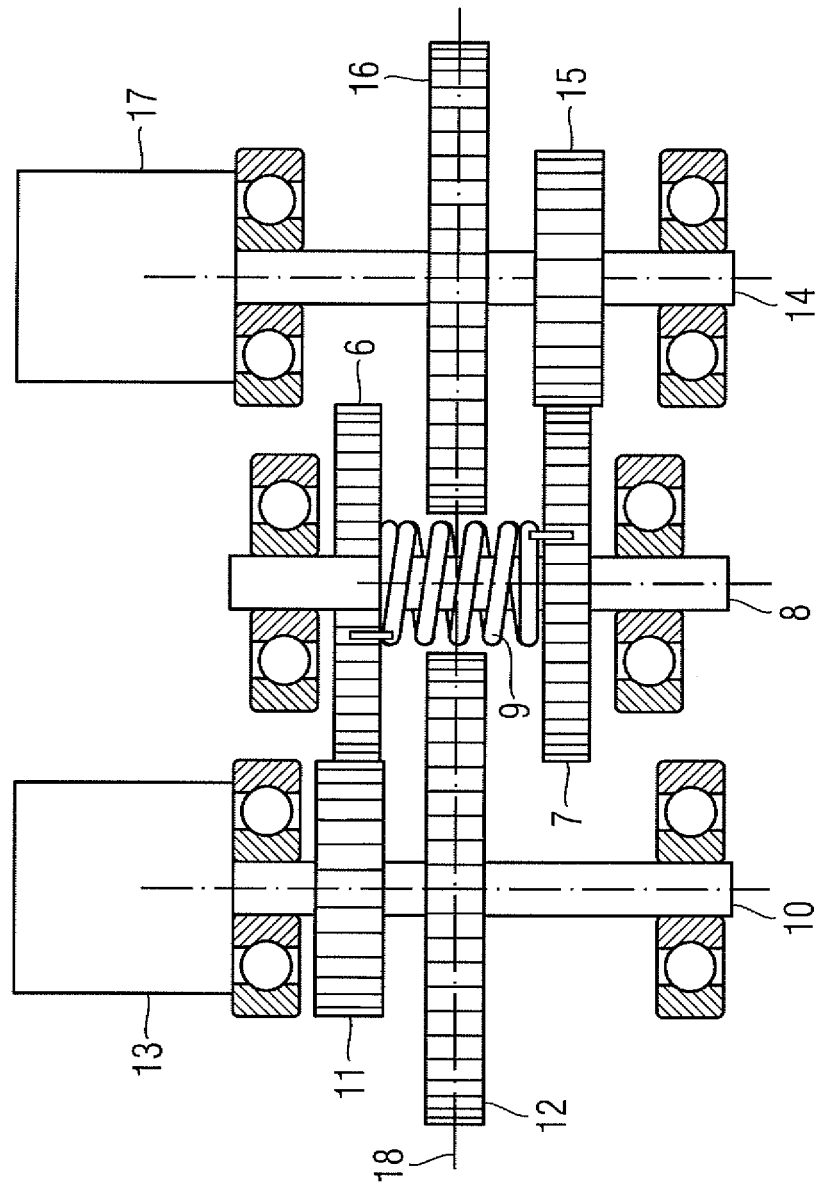
FIG. 2 shows one embodiment of an arrangement of a first rotational speed sensor and a second rotational speed sensor that are coupled via a connection device.

FIG. 2 shows a basic diagram of one embodiment of an arrangement of a first rotational speed sensor and a second rotational speed sensor that are coupled via a connection device. A first toothed wheel 6 and a second toothed wheel 7 are arranged on a first shaft 8. The first toothed wheel 6 and the second toothed wheel 7 are coupled via a pre-tensioned torsion spring 9. A third toothed wheel 11 and a fourth toothed wheel 12 are arranged on a second shaft 10. A first rotational speed sensor 13 sits on the second shaft 10 and is rigidly connected to the second shaft 10. The third toothed wheel 11 is coupled to the first toothed wheel 6. A play-free connection between the third toothed wheel 11 and the first toothed wheel 6 is established. A fifth toothed wheel 15 and a sixth toothed wheel 16 are arranged on a third shaft 14. A second rotational speed sensor 17 sits on the third shaft 14 and is rigidly connected to the third shaft 14. The fifth toothed wheel 15 is coupled to the second toothed wheel 7. A play-free connection between the fifth toothed wheel 15 and the second toothed wheel 7 is established. An X-ray detector (not shown) is attached to a pulley (not shown). The pulley includes a seventh toothed wheel (not shown) that is coupled to the fourth toothed wheel 12 and the sixth toothed wheel 16, such that teeth of the fourth toothed wheel 12 and of the sixth toothed wheel 16 rest permanently against teeth of the seventh toothed wheel as a result of the pre-tensioned torsion spring 9. Line 18 indicates a height, at which the fourth toothed wheel 12, the sixth toothed wheel 16, and the seventh toothed wheel are coupled. Pre-tensioning of the torsion spring 9 may be that the first rotational speed sensor 13 and the second rotational speed sensor 17 have a constant opposing moment at the height indicated by the line 18. Using this arrangement of the toothed wheels, the first rotational speed sensor 13 and the second rotational speed sensor 17 are coupled directly and without play to the pulley, to which the X-ray detector is attached. This provides that a violent jumping of the drive belt that connects a drive wheel to the pulley is to be detected by the first rotational speed sensor 13 and the second rotational speed sensor 17. Thus, the rotational position may be adjusted.

Figure 3:
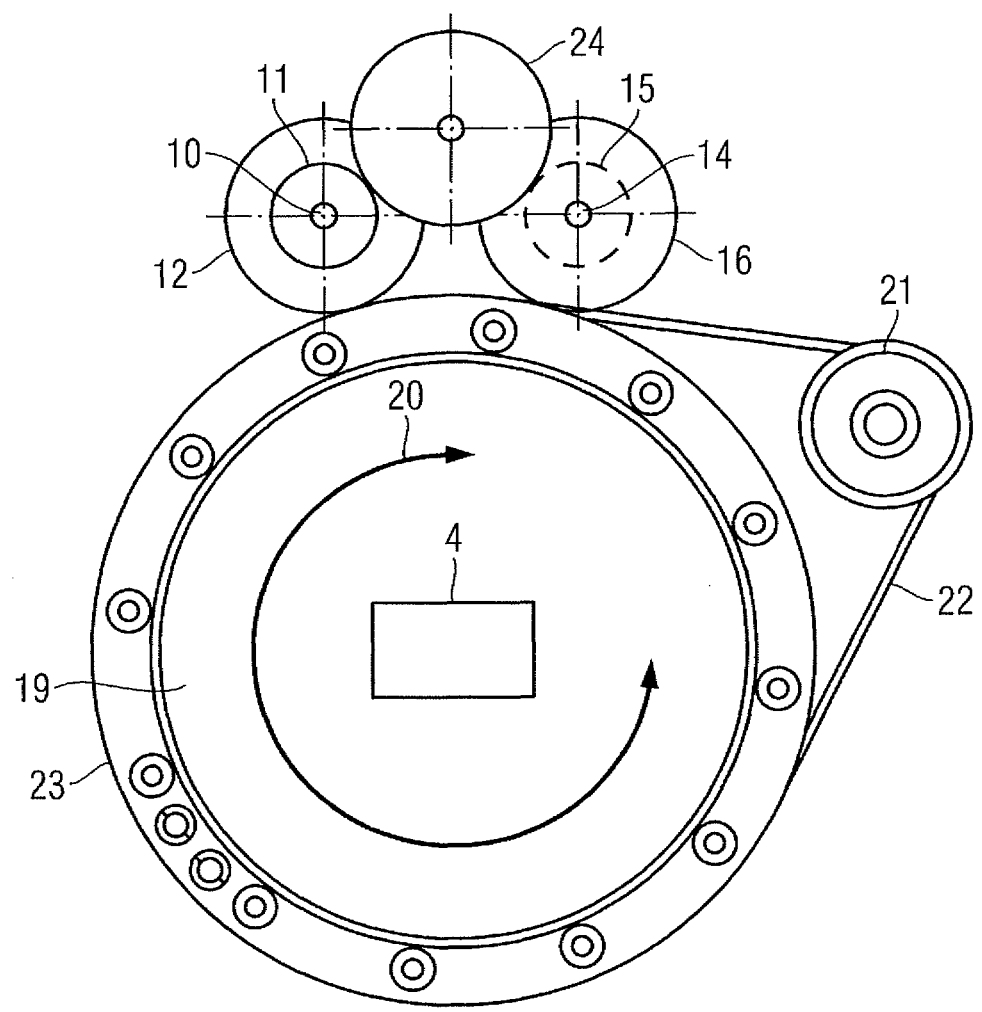
FIG. 3 shows one embodiment of an arrangement with a belt wheel driven by a rotation device.

FIG. 3 shows one embodiment of an arrangement with a pulley driven by a rotation device. A pulley 19, which has a direction of rotation 20 and to which an X-ray detector 4 is attached, is driven by a drive wheel 21 using a belt 22. The drive wheel 21 is driven by a motor not shown in FIG. 3. The pulley 19 includes a seventh toothed wheel 23. Teeth of the seventh toothed wheel 23 are arranged below a guide surface for the belt 22 on the outside of the pulley 19. The seventh toothed wheel 23 is coupled to a fourth toothed wheel 12 that is arranged around a second shaft 10, and to a sixth toothed wheel 16 that is arranged around a third shaft 14. A third toothed wheel 11, which is arranged around the second shaft 10, and the fifth toothed wheel 15, which is arranged around the third shaft 14, are coupled to a connecting device 24. The connecting device 24 includes a pre-tensioned torsion spring (not shown), a first toothed wheel (not shown), and a second toothed wheel (not shown). The third toothed wheel 11 is connected to the first toothed wheel (not shown), and the fifth toothed wheel 15 is connected to the second toothed wheel (not shown). A first rotational speed sensor (not shown in FIG. 3) sits on the second shaft 10, and a second rotational speed sensor (not shown) sits on the third shaft 14.

The seventh toothed wheel 23 is coupled to the fourth toothed wheel 12 and the sixth toothed wheel 16, such that teeth of the fourth toothed wheel 12 and of the sixth toothed wheel 16 rest permanently on teeth of the seventh toothed wheel 23 because of the pre-tensioned torsion spring not shown in FIG. 3. The pre-tensioning of the torsion spring provides that the first rotational speed sensor and the second rotational speed sensor have a constant opposing moment. Using this arrangement of the toothed wheels, the first rotational speed sensor and the second rotational speed sensor are coupled directly and without play to the pulley 19 to which the X-ray detector 4 is attached.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An arrangement comprising:
   an X-ray detector driven by a rotation device;
   a first rotational speed sensor and a second rotational speed sensor that determine a rotation of the X-ray detector;
   a pre-tensioned torsion spring; and
   a connection device comprising a first toothed wheel and a second toothed wheel, the first toothed wheel and the second toothed wheel being coupled via the pre-tensioned torsion spring,
   wherein the first rotational speed sensor and the second rotational speed sensor are coupled via the connection device to the pre-tensioned torsion spring,
   wherein the first rotational speed sensor comprises a third toothed wheel and a fourth toothed wheel, and
   wherein the third toothed wheel is coupled to the first toothed wheel.

2. The arrangement as claimed in claim 1, wherein the pre-tensioned torsion spring is pre-tensioned such that the first rotational speed sensor and the second rotational speed sensor have a constant opposing moment.

3. The arrangement as claimed in claim 1, wherein the second rotational speed sensor comprises a fifth toothed wheel and a sixth toothed wheel, and wherein the fifth toothed wheel is coupled to the second toothed wheel.

4. The arrangement as claimed in claim 3, wherein the fourth toothed wheel and the sixth toothed wheel are coupled to a pulley, to which the X-ray detector is attached.

5. The arrangement as claimed in claim 4, wherein the pulley comprises a seventh toothed wheel that is coupled to the fourth toothed wheel and the sixth toothed wheel such that teeth of the fourth toothed wheel and the sixth toothed wheel rest permanently against teeth of the seventh toothed wheel as a result of the pre-tensioned torsion spring.

6. The arrangement as claimed in claim 1, wherein the first rotational speed sensor comprises an absolute value sensor.

7. The arrangement as claimed in claim 1, wherein the second rotational speed sensor comprises a potentiometer sensor.

8. The arrangement as claimed in claim 4, wherein the first rotational speed sensor comprises an absolute value sensor.

9. The arrangement as claimed in claim 4, wherein the second rotational speed sensor comprises a potentiometer sensor.

* * * * *